(12) United States Patent
MacMorran et al.

(10) Patent No.: US 6,213,969 B1
(45) Date of Patent: *Apr. 10, 2001

(54) CARPEL TUNNEL SUPPORT

(76) Inventors: Ian MacMorran; Aurelia Koby, both of 2918 5th Ave., Ste 200, San Diego, CA (US) 92103

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/876,862
(22) Filed: Jun. 16, 1997
(51) Int. Cl.⁷ ..................................................... A61F 13/00
(52) U.S. Cl. .................................. 602/64; 602/5; 602/21; 602/62; 602/63
(58) Field of Search ....................................... 602/5, 20–22, 602/60–64; 128/877–880; 2/158–161.8; 473/59–62, 63, 190, 212, 213

(56) References Cited

U.S. PATENT DOCUMENTS

| | | | |
|---|---|---|---|
| 3,728,738 | * 4/1973 | Andolino | 2/161 |
| 4,854,309 | * 8/1989 | Elsey | 602/21 |
| 4,941,460 | * 7/1990 | Working | 602/21 |
| 5,160,314 | * 11/1992 | Peters | 602/21 |
| 5,375,278 | * 12/1994 | VanWinkle | 5/644 |
| 5,404,591 | * 4/1995 | Brinnard et al. | 2/20 |
| 5,810,753 | * 9/1998 | Eberbach | 602/21 |

* cited by examiner

*Primary Examiner*—Kim M. Lewis
(74) *Attorney, Agent, or Firm*—J. F. McLellan

(57) ABSTRACT

To address the problem of continuing work while suffering from possibly debilitating carpal; tunnel syndrome, a working wrist splint is provided to restrain the wrist joint to a therapeutically advantageous neutral position, yet allowing sufficient movement of the thumb and fingers to enable keyboard functioning. The form of the splint is a stretch fabric sleeve with a thumb opening, a finger aperture, a resiliently deformable wrist support ball at the bottom of the splint and a stiffening batten in a pocket at the top over the back of the wearer's hand.

10 Claims, 2 Drawing Sheets

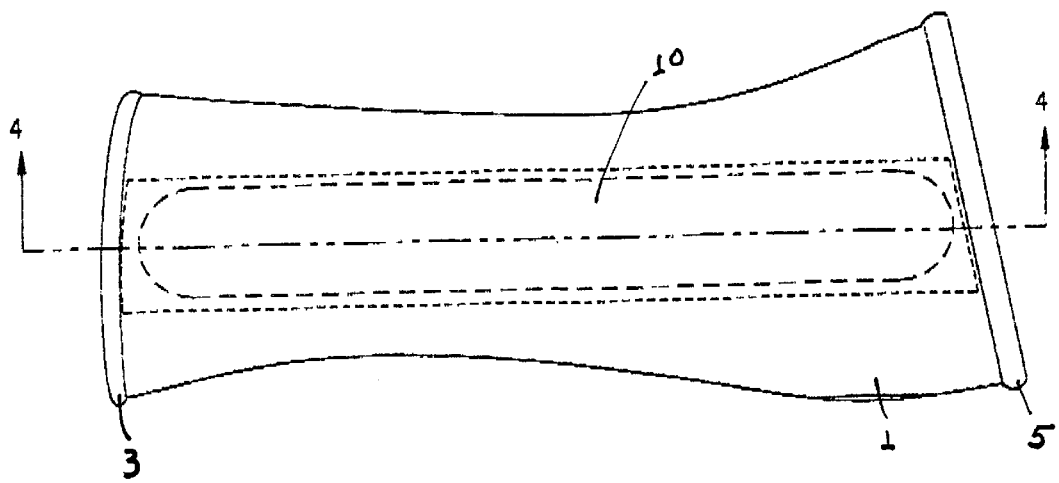
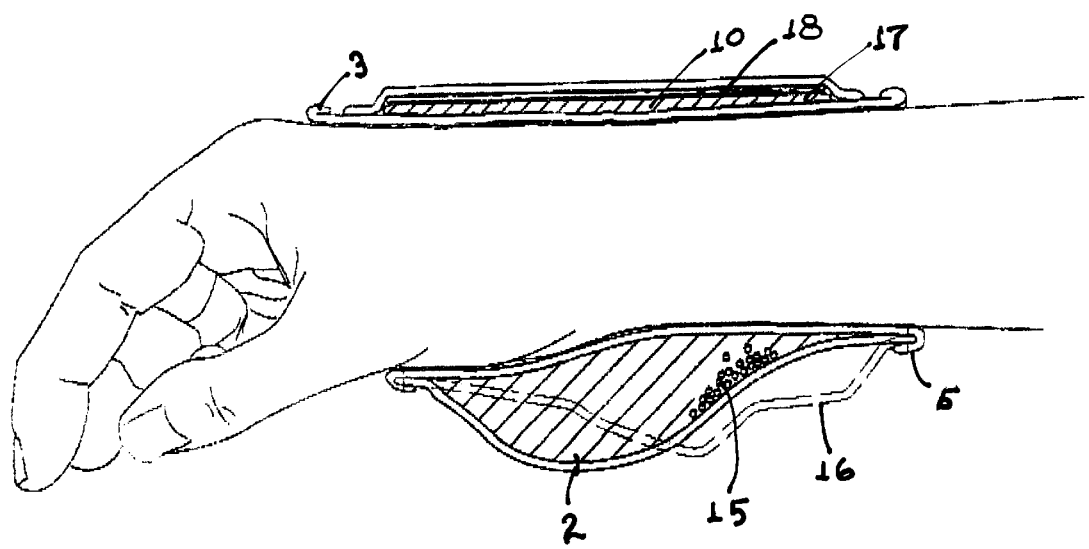

CARPEL TUNNEL SUPPORT

BACKGROUND OF THE INVENTION

Carpal Tunnel Syndrome (CTS) is a steadily increasing problem among workers who perform repetitive tasks generally, and among typists and other keyboard workers in particular. The pain resulting from injury to the median nerve and the nine tendons that pass through the bony passageway through the wrist can be excruciating, very difficult to treat and almost impossible to fully cure. Loss of productivity due to CTS among keyboard workers and even occasional keyboard users is estimated to be in the billions of dollars annually, and in some cases is so severe as to destroy a sufferer's ability to earn a livelihood at all.

A previous patent specification filed by one of the applicant inventors as U.S. Ser. No. 08/509491 described a resting arm splint that was proven efficacious in treatment of CTS by maintaining the wrist in a resting neutral position for extended periods of time at night, and contemplated that the wearer would regenerate hand and wrist functions through a resting period and then be able to remove the resting splint for a working period. In that invention, while effective for its design purpose, the bulk and extent of the semi-rigid battened splint from fingers to mid-forearm prevented sufficient movement of the hand and fingers to be operable in a working environment, and specifically would interfere with keyboard operation. The further development of the within invention addresses the need for a CTS treatment modality that can relieve pain by restraint of the wrist joint to a neutral position, yet be compact and light enough to enable working functionality at a keyboard. Further, appliance for this purpose should be comfortable enough to be worn for long periods in a working environment and be easily donned or doffed. Finally, if such a therapeutic appliance could be achieved, it would also operate as a preventive to further repetitive strain injury, and in some cases serve as a preventive if worn by a pre-injury user. While injured users may more readily be attracted to use of the within described carpel tunnel splint, the invention has been specifically designed to be attractive and comfortable in use so as to appeal to the pre-injury keyboardist, as it has been discovered that supporting and urging the wearer's hand and wrist to a neutral position is more comfortable and productive. In this regard, the carpel tunnel splint incorporates a stiffening batten that is necessary for therapeutic application to an injured user but optional to a pre-injury user, as that user finds the most comfortable mode of wear and usage in the operating environment. Comfort is an important consideration, since in the fast pace and urgency of the working environment, workers will shed uncomfortable, bulky or restrictive devices, no matter how therapeutic they may be.

While the majority of CTS complaints may result from keyboard work, other occupations also endure CTS or repetitive strain injuries and can benefit from the within invention. Contemplating other occupations, the device has been further designed to be adaptable to other working environments, in particular by replaceablility of the two elements of the appliance that support and stiffen the wrist, as the moldable wrist pad and the stiffening batten described later are contained in pockets in which other forms, sizes and resiliencies of material may be inserted.

FIELD OF THE INVENTION

The field of the instant invention is wrist support devices generally and carpal tunnel syndrome preventives specifically.

DESCRIPTION OF THE RELATED ART

Orthopedic restraint devices of many types and styles fill the annals of the prior art and commerce, some effective for some purposes and some not. Mere restrained movement is a primary treatment for any joint injury or pain, and the present invention seeks to extend this tradition of joint restraint. However particularized restraint to a specific position that best serves treatment of a particular joint on an individual sufferer must address precisely positioned restraint on a variety of sizes and shapes of human appendage, and this problem is compounded by the need to accommodate some movement in a working environment. Thus the device can strike a compromise between maximum restraint and user adjustable comfort, while still retaining a significant stiffness that will urge, not force, the user's wrist position to the neutral.

Many commercial products are now provided that claim CTS relief by merely wearing a close-fitting glove product that will put pressure on the joint and provide a modest limitation on movement, and these, while providing minor comfort, are generally ineffective to either relieve painful nerve contact within the carpal tunnel or prevent further repetitive stress injuries. Others limit movement more severely by straps, buckles and rigid brackets and stays, which are often uncomfortable and also limit working effectiveness unacceptably. In the patent literature, U.S. Pat. No. 5,404,591 to Brinnand exemplifies a well-intentioned but non-optimized glove-style product and mode of treatment. Brinnand includes a pad of material under the heel of the palm to rest and isolate the hand from a desk surface; however the glove does little to restrain wrist flexion and does not adjust in any meaningful fashion to particular positions of angular restraint that will relieve carpal tunnel nerve contact or pressure. Such a product does not address or provide any intervention or remedy for CTS.

Thus it is an objective of the within invention to provide a therapeutic wrist appliance that will allow sufficient hand and finger movement in a working environment.

Another objective of the invention is to restrain wrist movement in a carpal tunnel syndrome sufferer to a position that will relieve pressure on nerve and tendons in the carpal tunnel (neutral position).

Still another objective is to be adjustable over a range of angular restraint that will customize the appliance to specific positions found most relieving to an individual user.

Yet another objective is to provide a wrist appliance that is easily put on and removed in order to promote constant or at least frequent use in a working environment.

Another objective is to provide a wrist appliance that, with the batten removed, functions as a device to prevent wrist injury.

An additional objective is to provide an appliance that is fully adaptable to a keyboard working environment, including the ability to conveniently adapt to typical support requirements of the hand and forearm relative to a computer keyboard on a flat desktop.

Another objective is to provide an appliance which is fully adaptable to other types of work such as check-out clerks, by changing the described moldable pad to another support of different resiliency or stiffness, or by removing the batten.

These and other objectives are met by the invention summarized and described particularly below.

BRIEF SUMMARY OF THE INVENTION

Restraint of the wrist to the neutral position is critical to treatment and prevention of CTS. In the neutral position, the hand is aligned along the axis of the forearm and pronated, or rotated to the palm-down position. In this posture, the nerves and tendons passing through the carpal tunnel are free of contact with the bony enclosure of the tunnel and thus free from the primary source of abrasion, tension and resulting pain. One difficulty in achieving the neutral position is that it is inexactly defined and can be different for each sufferer, or even different as between the right and left hand of a single sufferer. Small angular movement or adjustments can be the difference between a fully neutral, relieved posture and a fully contacted, painful posture of the wrist. Thus each sufferer must find the neutral position by experimentation that best relieves pain, and thus an effective restraining appliance must accommodate a range of adjustments and retain the position found to be most effective by an individual wearer.

The instant invention achieves user restraint to the neutral positions by providing a specially configured glove-style carpel tunnel support that includes both a batten to stiffen the splint over the back of the hand and top of the wrist, and a pad in a pocket under the palm and heel of the wrist. The pad is preferably in the shape approximately of a ball or semi-spherical shape and deformable either by consisting of a relatively stiff rubber or foam material, or as in the described preferred embodiment, a sac filled with granular particles which will temporarily mold to and retain a shape when deformed by pressure of the user or the working environment.

The glove material is a stretch material that is resilient in two directions and can be provided in different degrees of spring strength. The combination of restraining features will allow movement of the fingers, and to a limited degree, the hand and wrist, and gently urge return of the enclosed joint to comfortable neutral position. The deformable nature of the moldable support palm ball, the fabric of the appliance itself and the slightly deflectable padded batten provides a gentle urging to the correct position rather than a rigid restraint which would destroy working functionality.

The moldable palm pad provides the primary degree of adjustability in that the resilient material that comprises the pad, such as plastic pellet form of granular filling material, can adjust not only to the shape of the user's angular wrist flexion that defines the maximum point of pain relief, but can also adjust to the environmental surface on which it will generally or occasionally be brought to rest, such as the edge of a desktop surface or the back edge of a computer keyboard. Also worthy of note is that the moldable wrist pad is also a substitute for other separate pads that are typically, but also ineffectively in many cases, employed to support the wrist for CTS pain relief, such as a rubber pad along the front edge of the keyboard or a separate pad at the pointing device (mouse) station. Thus the invention provides an additional benefit of supporting the user's entire forearm to promote the neutral wrist position as the hand is moved to various operational positions.

BRIEF DESCRIPTION OF THE DRAWINGS

FIG. 3 is a top view of the working carpel tunnel support with section lines indicating further view.

FIG. 4 is a section view of the working carpel tunnel support along line 4—4 of FIG. 3, showing the operator's hand and wrist restrained in a neutral resting position.

DETAILED DESCRIPTION OF THE INVENTION

Figure 1:
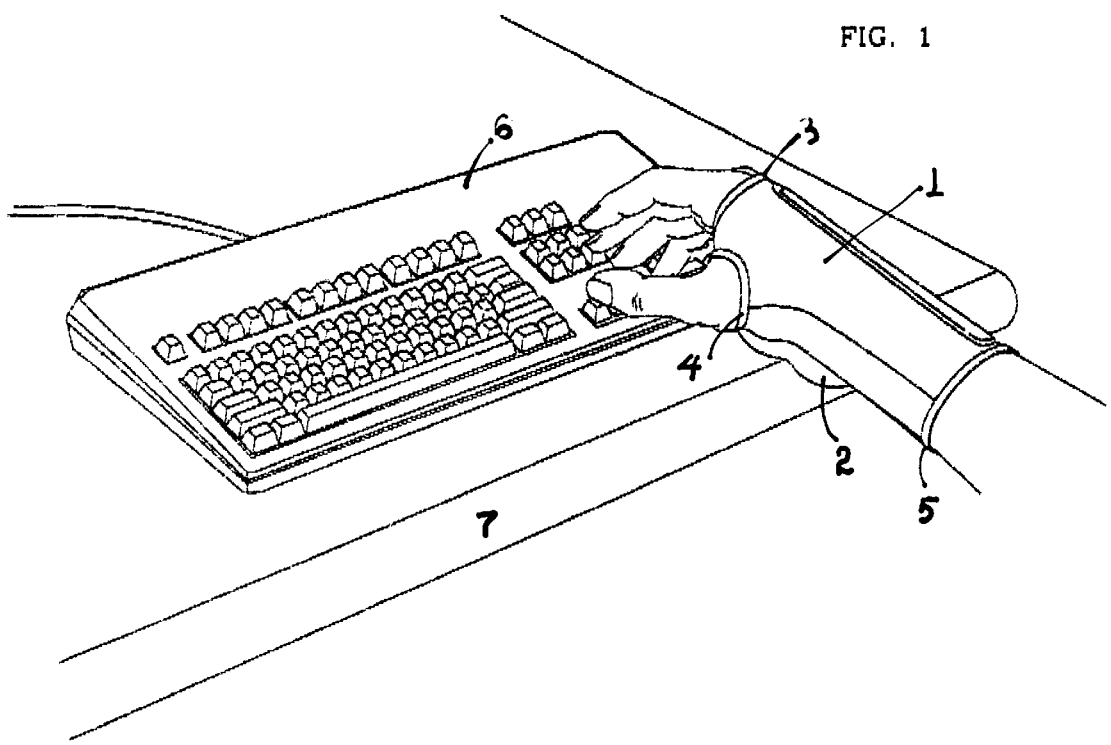
FIG. 1 is a perspective view of the working carpel tunnel support in use on an operator's hand, positioned typically at a keyboard on a desk surface.

With reference now to the drawings, FIG. 1 illustrates the keyboard working environment in which the present invention is designed to operate to the benefit of a typist or other keyboard worker who is already suffering from repetitive stress injury or wishes to prevent it. As the wearer is facing the keyboard 6, the splint appliance 1 on the wearer's right hand can be seen to extend about 6 to 7 inches from an aperture 3 at the front end just behind the knuckles through which the user's fingers protrude to an aperture 5 at the rear which surrounds the lower forearm. A thumb aperture 4 is provided at about the base of the thumb, allowing reasonably full operation of the thumb in opposition to the other digits of the hand. Support of the wrist from the bottom is provided by a deformable enclosed ball 2, shown here resting on the desk edge 7 comfortably and maintains the wrist in a neutral position found to be most pain-relieving by the wearer. It can also be seen here that the resting fulcrum provided by the ball or moldable pad urges the wrist to a slightly flexed position to the neural angle between hand and forearm that allows uncontacted passage in the carpal tunnel of the contained nerve and tendons.

FIG. 3 illustrates the construction of the appliance 1 as fabric sleeve (left-hand model with thumb aperture 4 positioned at the right side), having a forward aperture 3 banded by a sewn collar and a rearward aperture 5 also banded by a sewn collar. The forward aperture is here shown as an opening of sufficient width to allow all 4 fingers to protrude form the sleeve and extend to a working position, although the same effect could be obtained by configuring the forward aperture as two, three or four adjacent apertures for closer encirclement of the fingers separately (the term 'forward aperture' here intended to include both a single opening or up to four separate finger openings).

The appliance can be constructed in a variety of sizes to accommodate different groups of users, and as the fabric sleeve will stretch (limited stretch for ordinary fabric but a wider range of stretch movement for the preferred material which is double-stretch cotton fabric) the appliance can relatively easily be pulled over the user's hand and onto the wrist area, allowing the fingers to protrude fully from the forward aperture and function on the keyboard without significant restriction.

Figure 2:
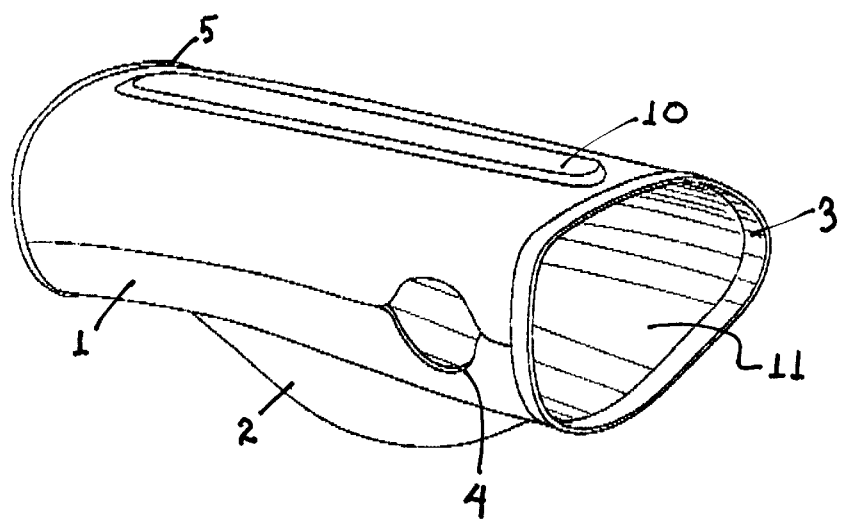
FIG. 2 is a perspective view of the working carpel tunnel support along.

It can also be seen in FIG. 2 that the moldable pad 2 is attached to the lower part of the fabric sleeve under the position of the palm and heel of the wrist. A fabric pocket forms the ball shape and is filled with resilient material such as foam rubber or pellet-type filling to provide a soft and comfortable support, yet be firm enough to fix the position of the wrist as it comes to the neutral position. The pad 2 thus constitutes a deformable pressure distribution pocket adapted to underlie and support the heel of the palm and the wrist portion, and projecting downwardly to space the heel of the palm, the forward aperture of the sleeve, and the wrist portion above the work surface upon engagement of the pocket with the work surface.

In some other applications and embodiments, such as the checkout clerk working environment mentioned above, the device may be constructed such that the fabric pocket which retains and encloses the moldable pad or ball may have an openable access such as a slit or flap (not shown in the preferred embodiment). Thus the user in an alternative environment may replace the moldable pad with another pad or filling material more suitable by being stiffer or more rigid or even removed altogether.

The wrist is further restrained within limits by a stiffener provided as an upper longitudinal pocket 10 which contains a batten. This batten stiffener restrains upward movement of the hand from the slightly flexed position necessary to achieve a neutral resting position for CTS relief. Further the fabric sleeve construction will also restrain rotational movement out of the desired pronated position of the hand 9 (supination) by torsional resiliency of the sleeve section extending between the area of the forearm aperture 5 and the finger aperture 3. The torsional resiliency of the fabric can be enhanced by the nature of the sleeve lining 11, which may be of a tack-type fabric that will not slip against the wearer's skin contact and tends therefore to return to the original wearing position rather than allow the wrist to slip around inside the sleeve. In all cases of restraint, the restraining force is not absolute nor is the appliance, rigid; instead the force gently urges the hand and wrist to a neutral position after it may become somewhat displaced from the position in the working operations directed to the keyboard.

FIG. 3 further illustrates the placement of the stiffening batten 12 inside the batten pocket 10, both running substantially the length of the sleeve appliance. Further in FIG. 4 cross section it may be seen that the batten 12 inside the batten pocket 110 is supplemented by a resilient material batten pad 17 which cushions the back of the wearer's hand from discomfortingly hard contact, serving again the objective of gently urging the hand and wrist into the neutral position rather than rigidly restraining it.

The batten pocket may also be constructed to be openable as by a slit or flap at one end. With such an opening, the batten can be removed and either replaced with one of differing stiffness or removed altogether for maximum allowed movement for users that do not require or desire the maximum support and restraint of the preferred embodiment.

Further in FIG. 4 in cross section, the shape and function of the moldable palm pad is illustrated. A ball shaped insert 2, within the fabric pocket that shapes and defines it, is composed of resilient volumetric filling material, here shown as the preferred mode of granular pellet-type filling 15, that declarant has found by extensive experimentation to be best provided by lenticular plastic pellets. The disc shape of the plastic pellets appears to provide an optimum cushioning effect by the deformability of rearrangements of the pellets due to pressure form above and below, yet the disc-like shape of the pellets retains an overall conformed shape well when the pressure is removed. This ability is illustrated by the shadow outline second position 16 of the ball pocket perimeter, which has responded to reshaping pressure of the edge of the desktop of FIG. 1 and at its upper surface has conformed to the exact shape and angular positioning of the wearer's palm and wrist juncture, retaining and urging return of the wearer's wrist joint to the neutral, most comfortable resting position after a working keyboard operation is completed.

The moldable pad support may also be seen in FIG. 1 as detailed by FIG. 4 to provide a substitute for other more generalized forms of wrist support such as a rubber keyboard or mouse pad, making the device effective especially in a keyboard working environment because it not only is therapeutic to the CTS sufferer but also conveniently enhances the working environment without need of other aids, orthotics or ergonomic devices. Of course, according to the user's needs and preferences, the invention and its supporting pad could also be used in conjunction with, rather than replacing, other supporting pads and cushions.

Thus it may be seen that the invention meets all of the objectives set for it above and includes further surprising results to the benefit of the wearer in a working environment. While further or constant restraint of the CTS sufferer's wrist joint may be desirable, greater restraint is available at non-working times by adoption of a splint types such as described in declarant's previous application that provides a full resting restraint at night, the instant invention providing similar restraint only slightly compromised to allow movement sufficient to attain effective function in the workplace. The CTS sufferer typically must employ as much rest and restraint as possible throughout the day and night, and the combination of the working described herein with other more rigidly restraining splints to be worn at other times provides that maximum application of relief.

What is claimed is:

1. A carpel tunnel support for use by a wearer in the operation of components located above a work surface, the support comprising:
    a flexible sleeve having a rearward aperture for admitting the hand of the wearer, particularly including the heel of the palm and the wrist portion adjacent to the hand, the sleeve further having a forward aperture for allowing the fingers of the hand to extend outwardly and downwardly in their relaxed state for movement between positions of engagement and disengagement relative to the components;
    a thumb aperture;
    an elongated batten attached to the upper side of the sleeve to resist upward movement of the hand; and
    a pad on the underside of the sleeve, the pad including a deformable pressure distribution pocket adapted to underlie and support the heel of the palm and the wrist portion, and projecting downwardly to space the heel of the palm, the forward aperture of the sleeve, and the wrist portion above the work surface upon engagement of the pocket with the work surface, thereby enabling the fingers in their relaxed state to extend for engagement and disengagement of the components on the work surface.

2. A carpel tunnel support according to claim 1 and including an elongated batten attached to the upper side of the sleeve to resist upward movement of the hand.

3. A carpel tunnel support according to claim 2 and including a resilient cushioning layer between the batten and the sleeve.

4. A carpel tunnel support according to claim 1 wherein the pocket contains material which is deformable upon engagement of the pocket with the work surface thereby to substantially prevent slidable movement of the pocket relative to the work surface.

5. A carpel turned support according to claim 4 wherein the material within the pocket comprises a multiplicity of pellets movable relative to one another.

6. A carpel tunnel support according to claim 5 wherein the pellets are disk shaped.

7. A carpel tunnel support according to claim 4 wherein the material within the pocket is foam rubber.

8. A carpel tunnel support according to claim 1 wherein the pocket is also resilient.

9. A carpel tunnel support according to claim 1 wherein the forward aperture is formed by the sleeve, and the sleeve divides the forward aperture into a plurality of apertures for the fingers of the hand.

10. A carpel tunnel support according to claim 1 wherein the material of the sleeve comprises a double stretch resilient fabric.

* * * * *

UNITED STATES PATENT AND TRADEMARK OFFICE
CERTIFICATE OF CORRECTION

PATENT NO. : 6,213,969 B1
DATED : April 10, 2001
INVENTOR(S) : Ian MacMorran; Aurelia Koby It is certified that error appears in the above-identified patent and that said Letters Patent is hereby corrected as shown below:

Column 1,
Line 39, delete "splint" and insert -- support --;
Line 44, delete "splint" and insert -- support --;

Column 5,
Line 45, delete "form" and insert -- from --; and

Column 6,
Line 11, after "working" insert -- carpel tunnel support --.

Signed and Sealed this

Sixth Day of November, 2001

*Attest:*

NICHOLAS P. GODICI
*Attesting Officer*     *Acting Director of the United States Patent and Trademark Office*